United States Patent [19]

Kaufman

[11] Patent Number: 5,396,075
[45] Date of Patent: Mar. 7, 1995

[54] METHOD FOR IN SITU CHARACTERIZATION OF A MEDIUM OF DISPERSED MATTER IN A CONTINUOUS PHASE

[75] Inventor: Eric N. Kaufman, Knoxville, Tenn.

[73] Assignee: The United States of America as represented by the United States Department of Energy, Washington, D.C.

[21] Appl. No.: 97,190

[22] Filed: Jul. 27, 1993

[51] Int. Cl.⁶ ..................... G01N 21/64; G01N 21/85
[52] U.S. Cl. .................. 250/459.1; 250/302; 250/356.1; 250/359.1; 250/458.1
[58] Field of Search ............... 250/459.1, 458.1, 461.1, 250/461.2, 255, 359.1, 356.1

[56] References Cited

U.S. PATENT DOCUMENTS

| | | | |
|---|---|---|---|
| 3,501,639 | 3/1970 | Monroe | 250/461.1 |
| 3,839,639 | 10/1974 | Hughes | 250/302 |
| 3,918,812 | 11/1975 | Holm | 250/459.1 |
| 4,515,896 | 5/1985 | Melton | 250/356.1 |
| 4,564,598 | 1/1986 | Briggs | 250/459.1 |
| 4,959,549 | 9/1990 | Haub et al. | 250/461.1 |
| 5,047,632 | 9/1991 | Hunt | 250/259 |
| 5,225,675 | 7/1993 | O'Donnell | 250/459.1 |

FOREIGN PATENT DOCUMENTS

458741 1/1975 U.S.S.R. ........................ 250/461.1

OTHER PUBLICATIONS

Coethoso, I, et al., "Biofilm Reactors: An Experimental and Modeling Study of Wastewater Denitrification in Fluidized-Bed Reactors of Activated Carbon Particles." Biotechnology and Bioengineering, 1992. 40: pp. 625–633.

Rowe, P. N. et al, "The Mechanisms of Solids Mixing in Fluidised Beds." Transactions of the Institution of Chemical Engineers, 1965. 43: pp. T271–T286.

Kurosaki, Y. et al, "Mechanisms of heat transfer enhancement of fluidized bed: estimation of direct contact heat exchange from heat transfer surface to fluidized particles by using an optical visualization technique."

ASME/JSME Thermal Engineering Proceedings, 1991 4: pp. 465–472.

Hacek, A, et al. "Characterization of solids mixing in a laboratory scale fluidized bed" Proceedings of the Advanced Research and Technology Development Direct Utilization Contractors Review Meeting. 1985. Morgantown, W.V.: U.S. Department of Energy.

Chen, M. M., et al. "Collaborative research on fluidization employing computer aided particle tracking." Proceedings of the Advanced Research and Technology Development Direct Utilization, Instrumentation and Diagnostics of Axial Mixing Coefficients. Chemical Engineering Science, 1968. 23. pp. 825–831

Van Der Meer, A. P. et al, "Mixing of Particles in Liquid Fluidised Beds." Chem. Eng. Res. Des. 1984. 62: pp. 214–222.

De Felice, R. et al, "Mixing and Segregation in Binary-Solid Liquid Fluidised Beds." Chemical Engineering Science, 1987. 42(4): pp. 639–652.

Hemati, M. et al, "Experimental Study of Sawdust and Coal Particle Mixing in Sand or Catalyst Fluidized Beds." The Canadian Journal of Chemical Engineering, 1990. 68 pp. 768–772.

Kececioglu, I. "Computation of Solid Circulation Rates in a Fluidized Bed from Tracer Particle Concentration Distributions." The Canadian Journal of Chemical Engineering. 1986 67: pp. 290–300.

(List continued on next page.)

Primary Examiner—Carolyn E. Fields
Attorney, Agent, or Firm—Emily C. Green; Stephen D. Hamel; William R. Moser

[57] ABSTRACT

A method for in situ characterization of a medium of a dispersed phase in a continuous phase, including the steps of adding a fluorescent dye to one phase capable of producing fluorescence therein when the fluorescent dye is optically excited, optically exciting the fluorescent dye at a wavelength to produce fluorescence in the one phase, and monitoring the fluorescence to distinguish the continuous phase from the dispersed phase.

7 Claims, 1 Drawing Sheet

OTHER PUBLICATIONS

Shor, J. T. et al, "The Sedimentation of Biomodal Distributions of Unflocculated Microspheres." Separation Science and Technology, 1990, 25: pp. 2157–2170.

Scott, T. C., et al, "Hydrodynamic Studies of an Advanced Fluidized-Bed Bioreactor for Direct Interaction with Coal." Fuel Dec. 1993, pp. 1701–1704.

Grbavcic, Z. B. et al, "Tracer Particle Movement in a Two-Dimensional Water FLuidized Bed." Powder Technology, 1990. 62: pp. 199–201.

Grbavcic, Z. B. et al, "Single Particle Settling Velocity Through Liquid Fluidized Beds" Powder Technology, 1991. 66 pp. 293–295.

Grbavcic, Z. B., et al. "The effective buoyancy and drag on spheres in a water-fluidized bed." Chemical Engineering Science, 1992 . 47(8) pp. 2120–2124.

Yamazaki, H. et al, "Measurement of Local Solids Concentration in a Suspension by an Optical Method." Powder Technology, 1992. 70: pp. 93–96.

Holdich, R. G., et al "Measurement of Slurry Solids Content by Electrical Conductivity." Powder Technology, 1992. 72: pp. 77–87.

Halow, J. S., et al. "Observations of Fluidized Bed Coalescence Using Capcitance Imaging." Powder Technology, 1992. 69 pp. 255–277.

Li, H. et al, "Micro-Visualization of Clusters in a Fast Fluidized Bed." Powder Technology, 1991. 66: pp. 231–235.

Rhodes, M., et al "Particle Motion at the Wall of a Circulating Fluidized Bed." Powder Technology, 1992. 70: pp. 207–214.

Song, G. H. et al, "Image Processing Technique for Measurement of Solids Holdup in Near Wake Behind a Single Bubble in a Liquid–Solid Fluidized Bed." Chemical Engineering Science, 1991. 46(11): pp. 2933–2941.

METHOD FOR IN SITU CHARACTERIZATION OF A MEDIUM OF A DISPERSED MATTER IN A CONTINUOUS PHASE

The United States Government has rights in this invention pursuant to Contract No. DE-AC05-84OR21400 with Martin Marietta Energy Systems, Inc., awarded by the U.S. Department of Energy.

BACKGROUND OF THE INVENTION

This invention relates generally to characterizing dispersed matter in a continuous phase and more specifically to a method for in situ characterization of a medium of dispersed matter in a continuous phase.

In fluidized beds, droplet coalescence chambers, well mixed batch reactors, fermentation reactors, and other such systems, it is desirable to characterize the size, distribution, or flow of dispersed matter in the continuous phase contained in the reactor system. A variety of techniques exist in which the dispersed matter is physically removed from the system and sized and sorted using conventional methods. These techniques, however, are invasive, since the act of particle sampling may disturb the size, distribution, or flow characteristics of the dispersed matter and the reactor system. Other methods involve "tracer" techniques in which a subclass of the dispersed matter is altered to facilitate its detection. Examples of these methods include radiolabelling of particles, painting the particles with fluorescent paint, and using particles of a different color or size. These techniques are also considered invasive because the physical characteristics of the dispersed phase are changed. Furthermore, the systems represented by these methods are often specialized cases and do not represent the population size, chemistry, or other characteristics occurring in the actual operating reactors. Because of these deficiencies, current techniques cannot be utilized to monitor operating systems.

Although noninvasive methods are available, they may not be used in systems containing a high dispersed phase content and do not provide fine spatial resolution. For extremely dilute systems (<1%), the dispersed phase may be visualized directly, or light scattering techniques may be employed. Capacitance measurements provide dispersed phase volume fraction in more dense systems, and capacitance imaging has been used to study bubble flow and coalescence in gas fluidized beds. Current capacitance imaging, however, is limited in resolution to objects of the order of 1 cm. Finally, video techniques used to observe particle flow in fluidized beds are also known, but while such techniques provide images at solid volume fractions up to 40%, they have disclosed only macroscopic information and have not been used to characterize individual particles.

Accordingly, a need in the art exists for an in situ method for characterization of a medium of dispersed matter in a continuous phase which is noninvasive, enables direct characterization of dispersed matter in a continuous phase at virtually any volume fraction, and provides fine spatial resolution.

SUMMARY OF THE INVENTION

In view of the above need, it is an object of this invention to provide a method for characterization of a medium formed of a dispersed phase in a continuous phase.

Another object of this invention is to provide a method as in the above object that is noninvasive.

Further, it is an object of this invention to provide a method as in the above objects that may be used in situ in actual operating reactors.

It is another object of this invention to provide a method as in the above objects which enables direct characterization of dispersed matter in a continuous phase at virtually any volume fraction.

Still another object of this invention is to provide a method as in the above objects which provides fine spatial resolution.

Briefly, the present invention is a method for in situ characterization of a medium of dispersed phase in a continuous phase, comprising the steps of: adding a fluorescent dye to one of the phases of the medium capable of producing fluorescence therein when the fluorescent dye is optically excited, optically exciting the fluorescent dye at a wavelength to produce fluorescence in the one phase, and monitoring the fluorescence to distinguish the continuous phase from the dispersed phase.

One aspect of the present invention comprises the steps of: adding a fluorescent dye to the continuous phase capable of producing fluorescence only in the continuous phase when the fluorescent dye is optically excited, optically exciting the fluorescent dye at a wavelength to produce fluorescence in the continuous phase, and monitoring the fluorescence to distinguish the continuous phase from the dispersed matter which appears as dark regions on an otherwise brightly fluorescent continuous phase background.

In accordance with another aspect of the invention, the fluorescent dye may be added to the dispersed phase depending upon the system chemistry.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and form a part of the specification, illustrate preferred embodiments of the invention and, together with the description, serve to explain the principles of the invention.

DETAILED DESCRIPTION

Figure 1:
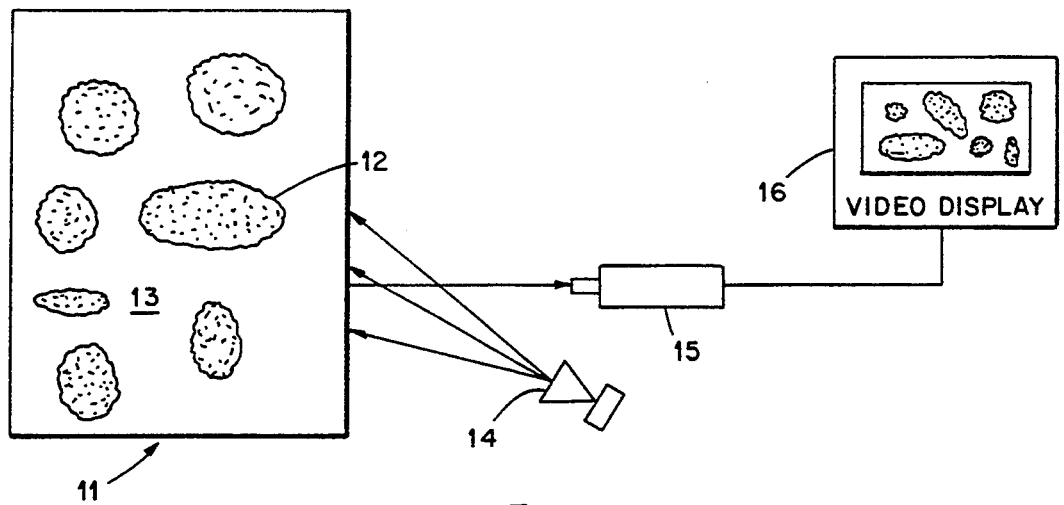
FIG. 1 is a schematic diagram illustrating the method of characterizing a medium of dispersed matter in a continuous phase according to the present invention.

Referring to FIG. 1, a medium 11 formed of dispersed matter 12 in a continuous phase 13 is shown. A fluorescent dye capable of producing fluorescence only in the continuous phase is added to the medium 11 to produce fluorescence when optically excited. Next, the dye is excited by directing a beam of light from a light source 14 onto at least a portion of the medium 11 at an appropriate wavelength to excite fluorescence in the continuous phase. Fluorescence emitted from the continuous phase 13 is monitored by means of a video camera 15 to distinguish the continuous phase 13 from the dispersed matter 12 which appears as dark regions on an otherwise brightly fluorescent continuous phase background. Selected images may be observed on a video display 16 in a still frame to characterize the size, distribution, or movement of the dispersed matter 12 in the medium 11. Further, the images may be stored on videotape for later playback and analysis, as will be shown with reference to the system used to test the invention in accordance with the following example.

EXAMPLE I

Figure 2:
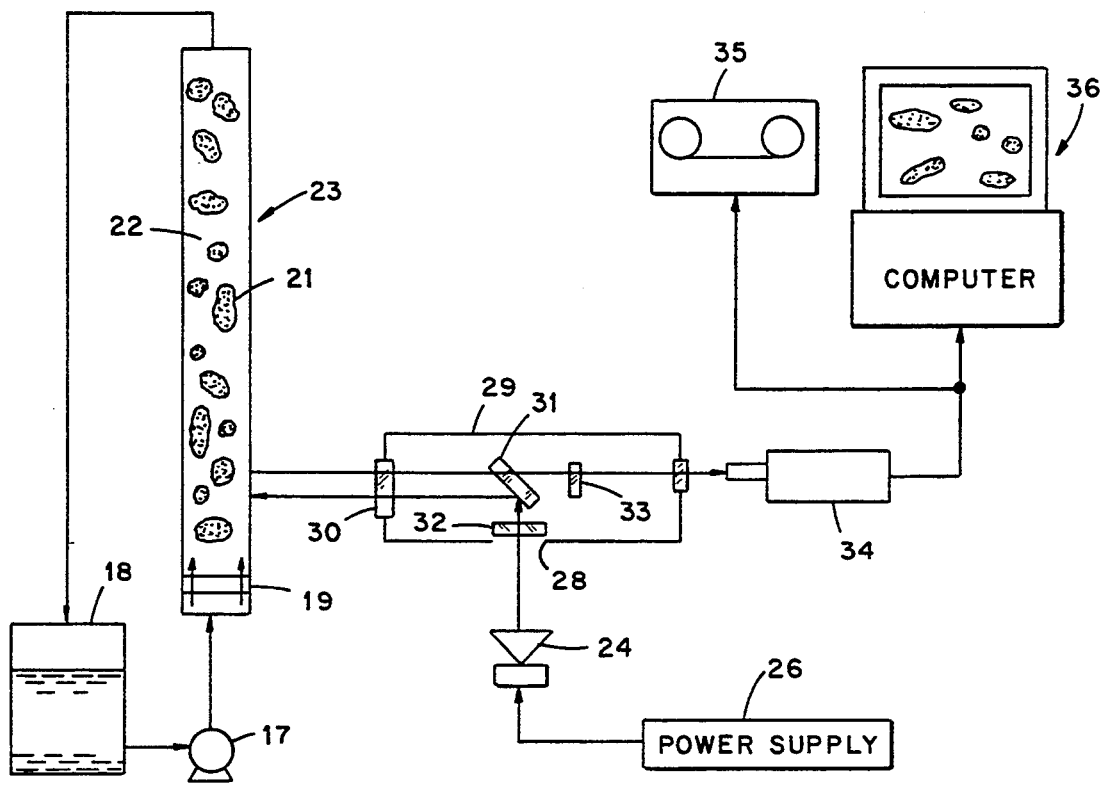
FIG. 2 is a schematic diagram illustrating an example of the application of the present invention to the characterization of coal particles in a liquid fluidized bed column.

Referring to FIG. 2, the method of the present invention was used to characterize a slurry of coal particles 21 dispersed in an aqueous solution 22 contained in a liquid fluidized bed column 23. The coal slurry was made by fluidizing Illinois #6 coal, in the size range of about 25 to 250 μm, with water and the surfactant Tween 80 (polyoxyethylene) (J. T. Baker, Inc., Phillipsburg, N.J.) and pumped through the column 23 using a pump 17 communicating with a liquid feed reservoir 18. The reservoir 18 was connected to receive the liquid effluent from the column 23. The column 23 consisted of four, one foot sections of glass pipe with a one inch diameter and was fitted with a coarse glass frit 19 at the column base to contain the solid particles 21. The fluorescent dye fluorescein (FX325 L395 Matheson Coleman & Bell, Norwood, Ohio) was added to the water to a concentration of about 0.33 grams per liter. Light from a 100 W Hg bulb 24 (#6281 Oriel) housed in an appropriate lamp source (#60063 Oriel, Stratford, Conn.) (not shown) and powered by a stable power supply 26 (#60012 Oriel) was used to excite fluorescence in the continuous phase. The excitation light passed through the epi-illumination port 28 of a Ziess universal microscope head 29 (Carl Ziess Inc., Hanover, Md.) and was directed onto to the column 23 using a dichroic mirror 31 (#487709 Carl Ziess, Inc.) housed in the microscope head 29. The microscope head 29 was removed from its conventional support arm and was rotated 90 degrees so that the 6.3× objective 30 (#2157197 Carl Ziess, Inc.) of the microscope head 29 was perpendicular to the wall of the fluidized bed column 23. The proper excitation wavelength for the fluorescein dye was selected using a fluorescein filter 32 (#487709 Carl Ziess, Inc.) housed in the microscope head 29. Subsequent to this filtering, the light was focused onto the specimen using the objective 30. The focused excitation light, at a wavelength of about 480 nm, impinged the sample and excited the dye in the continuous phase to produce fluorescence emitted at a wavelength of about 520 nm. The dispersed coal particles 21 lacked detectable fluorescence at this wavelength and appeared as dark regions on the brightly fluorescent continuous phase background. Fluorescence emitted from the specimen was collected through the same objective 30 used to focus the excitation light to ensure proper alignment of the lamp source and the most efficient collection of the emitted fluorescence. The emitted fluorescence passed through the dichroic mirror 31, and light below about 500 nm was removed using a long pass filter 33 (#487709 Carl Ziess, Inc.). After passing through the filter 33, the fluorescent signal was imaged using a video camera 34 (Xybion SVC-11, Xybion Electronic Systems Corp., San Diego, Calif.) mounted to the microscope using an extension tube (#473023-9900 Carl Ziess, Inc.) and a 1× camera coupler (HR100-CMT Carl Ziess, Inc.) (not shown). The images were recorded using a VCR 35 (AG-1960, Panasonic Industrial Co., Secaucus, N.J.) and analyzed using a video frame grabber 36 (DT2867, Data Translation, Marlboro, Mass.) and appropriate prepackaged software (Global Lab, v2.0, Data Translation).

The spatial resolution of the application of the present invention shown in FIG. 2 may be changed by using a microscope objective of a different order of magnification. In addition, the amount of fluorescein dye added may be varied in order to change the degree of contrast between the dispersed phase and the continuous phase.

The method of the present invention shown in FIG. 1 may be useful in several different applications. This technique may be used in gas/liquid fluidized bed reactors to characterize gas bubbles dispersed in a continuous liquid phase. In addition, it may be necessary to add dye to the dispersed phase rather than to the continuous phase. For example, droplets of one solution dispersed in another solution may be characterized as in coalescence chambers, emulsion phase contactors, and aerosol and nozzle research. Furthermore, this concept may be used to examine the morphology of mammalian and plant cells, bacteria, or fungi growing in culture vessels, or to study the flow of a liquid phase through a solid media such as soil or concrete.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A method for in situ characterization of a coal slurry medium containing a coal particle dispersed phase in an aqueous solution continuous phase, comprising the steps of:

adding a fluorescent dye to said continuous phase capable of producing fluorescence only in said continuous phase when said fluorescent dye is optically excited;

optically exciting said fluorescent dye at a wavelength to produce fluorescence in said continuous phase; and imaging said fluorescence to optically view said dispersed matter in said continuous phase, said dispersed matter appearing as dark regions on an otherwise brightly fluorescent continuous phase background to thereby characterize the size, distribution, or movement of said dispersed matter in said continuous phase.

2. The method as set forth in claim 1, wherein said fluorescent dye is fluorescein.

3. The method as set forth in claim 2, wherein said fluorescein is added to said continuous phase to a concentration of about 0.33 grams per liter.

4. The method as set forth in claim 3, wherein said step of optically exciting said fluorescent dye includes directing a beam of light onto at least a portion of said medium at a wavelength capable of exciting said dye in said continuous phase to produce fluorescence therein.

5. The method as set forth in claim 4 wherein said wavelength capable of exciting said dye in said continuous phase is about 480 nm.

6. The method as set forth in claim 5, wherein said fluorescence emitted from said continuous phase is at a wavelength of about 520 nm.

7. The method as set forth in claim 6, wherein said coal particles dispersed in said continuous phase are in a range of from about 25 to 250 μm.

* * * * *